(12) United States Patent
Handa et al.

(10) Patent No.: US 6,458,949 B1
(45) Date of Patent: Oct. 1, 2002

(54) CEFTIOFUR, ITS INTERMEDIATE AND A PROCESS FOR THE PREPARATION OF THE SAME

(75) Inventors: Vijay Kumar Handa; Meenakshisunderam Sivakumaran; Ramesh Dandala; Venkataiah Sunku, all of Hyderabad (IN)

(73) Assignee: Aurobindo Pharma Limited, Hyderabad (IN)

( * ) Notice: Subject to any disclaimer, the term of this patent is extended or adjusted under 35 U.S.C. 154(b) by 0 days.

(21) Appl. No.: 09/902,513

(22) Filed: Jul. 9, 2001

(30) Foreign Application Priority Data

Aug. 14, 2000 (IN) ...................................... 646/MAS/2000

(51) Int. Cl.$^7$ ............................................. C07D 501/36
(52) U.S. Cl. ........................................ 540/226; 540/227
(58) Field of Search .................................. 540/226, 227

(56) References Cited

U.S. PATENT DOCUMENTS 4,464,367 A * 8/1984 Labeeuw et al. ........... 514/206
5,158,946 A * 10/1992 Gasson et al ............... 514/201

\* cited by examiner

*Primary Examiner*—Mark L Berch
(74) *Attorney, Agent, or Firm*—Jay Akhave

(57) ABSTRACT

A novel process for the preparation of ceftiofur, a cephalosporin antibiotic useful in the treatment of bovine respiratory disease using a novel bromo or chloro intermediate. the process comprises of the steps of cyclizing a new bromo or chloro intermediate with thiourea in the presence of selected solvents to produce ceftiofur of high purity. A process to prepare such novel bromo and chloro intermediate comprising of the steps of condensing silylated Furaca with 4-(bromo or chloro)-2 methoxyamino-3-oxobutyric acid or its acid halide is also described.

9 Claims, No Drawings

CEFTIOFUR, ITS INTERMEDIATE AND A PROCESS FOR THE PREPARATION OF THE SAME

BACKGROUND OF THE INVENTION

The present invention relates to ceftiofur, its intermediate and preparation of ceftiofur. This invention relates to a new method of preparation of syn 7-[2-(amino-1,3-thiazol-4-yl)-2-(methoxyimino)acetamido]-3-[2-furylcarbonylthiomethyl]-3-cephem-4-carboxylic acid, also known as ceftiofur, of the formula

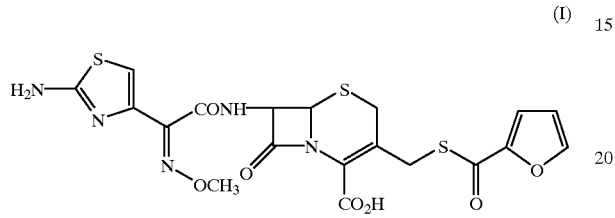

(I)

which is a cephalosporin antibiotic useful in treating bovine respiratory disease.

1. Field of the Invention

This invention describes the preparation of ceftiofur starting from 7-amino-3-(2-furylcarbonylthiomethyl)-3-cephem-4-carboxylic acid, hereafter called as Furaca of the formula

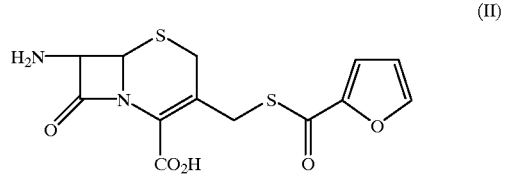

(II)

through an open side chain route where the formation of the thiazolyl ring of ceftiofur is achieved in the final step.

2. Description of the Related Art

U.S. Pat. No. 4,464,367 by Labeeuw teaches a process of preparation of ceftiofur. Ceftiofur was synthesized by condensing activated syn isomer of (2-tritylamino-4-thiazolyl)-2-methoxyimino acetic acid of the formula

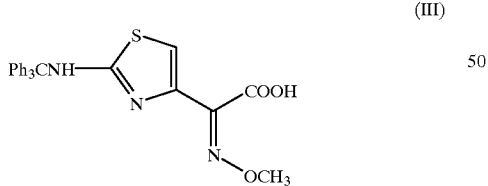

(III)

with Furaca in presence of triethylamine to yield tritylceftiofur which on further treatment with aqueous formic acid yielded ceftiofur.

U.S. Pat. No. 5,583,216 by Takeda Chemical Industries Ltd. teaches a process to prepare cephem compounds and claims an acylation whereby (2-amino-4-thiazolyl)-2-methoxyiminoacetyl group is introduced on the 7-amino group of a cephem moiety.

It is well known in the literature that the thiazole ring formation as a final step has been used for the preparation of cephalosporin antibiotics but there are no reports yet to date for the preparation of Ceftiofur by such a methodology. It is probable that no one to date has developed such a route and that the yields are either generally considered low and have failed to be reported. U.S. Pat. Nos. 4,458,072 and 4,482,710 are included here as reference.

BRIEF SUMMARY OF THE INVENTION

The present invention provides a novel method of preparation of ceftiofur in high yield from Furaca comprising of the following steps:

(a) condensation of 4-bromo-2-methoxyimino-3-oxobutyryl chloride with silylated Furaca (b) the isolation of the resulting product
7-[4-Bromo-2-methoxyimino-3-oxobutyramido]-3-[2-furylcarb onylthiomethyl]-3-cephem-4-carboxylic acid of the formula

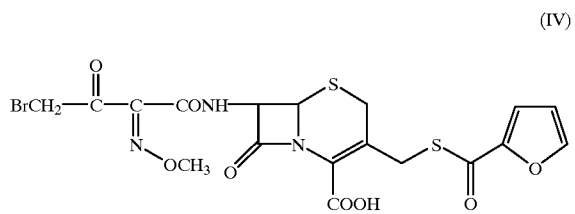

(IV)

in pure form and referred to as the bromo intermediate (c) Cyclization of the bromo intermediate to yield ceftiofur

DETAILED DESCRIPTION OF THE INVENTION 4-bromo-2-methoxyimino-3-oxobutyric acid of the formula

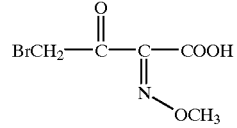

is a key intermediate in the present invention, and is prepared in high purity and good yield starting from tert-butyl acetoacetate (Ref U.S. Pat. No. 5,095,149). Tert-butylacetoacetate has been prepared from tert-butylacetate per Organic Synthesis Coll. Vol.-V, p-156 and references cited therein. This is converted into a corresponding acid chloride of the formula

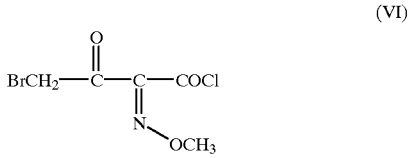

(VI)

by using halogenating agents such as oxalyl chloride, phosphorous pentachloride, phosphorous oxychloride, etc. Acid chloride may be isolated prior to condensation with a cephem moiety or may be generated in situ and used as such.

Acid chloride of formula VI is reacted with a silylated Furaca in a suitable solvent(s). Suitable solvents include methylene chloride, N,N-Dimethylformamide, N,N-Dimethylacetamide, acetonitrile, toluene or mixtures thereof. Particularly preferred solvent is methylene chloride. Silylation of Furaca is effected using silylating agents such as Hexamethyl disilazane, Trimethylsilyl chloride, Bistrimethylsilyl urea, N,O-Bistrimethylsilyl acetamide or monotrimethylsilyl acetamide in the presence of a catalysts such as acetamide and imidazole. Choice of silylation conditions and silylating reagent is found by us to be critical for achieving the desired purity during condensation with acid chloride of Formula (VI). It is observed by us that the monotrimethylsilyl acetamide in methylene chloride at 20–25° C. silylates Furaca in 1 hour. Longer periods during silylation leads to impurities which are subsequently very difficult to eliminate during workup and further contaminate the finished product. Imidazole has been found to be the catalyst of choice in the silylation step.

Condensation of the compound of formula VI with silylated Furaca gives the bromo intermediate of formula IV. The bromo intermediate of formula IV is cyclized in-situ with thiourea in the presence of sodium acetate. However the ceftiofur obtained is impure and further purifications are difficult, time consuming and do not result in a product of good quality. We have found that surprisingly the bromo intermediate of the formula IV is not reported in the literature and hence constitutes the novelty of our invention. The present inventors have also found that the bromo compound of formula IV can be isolated in pure form and only this pure form of the compound gives ceftiofur of high purity after cyclization with thiourea. Isolation of the bromo intermediate forms the inventive step of our process.

In a further aspect of the present invention 7-[4-chloro-2-methoxyimino-3-oxobutyramido]-3-[2-furylcarbonylthiom ethyl]-3-cephem-4-carboxylic acid of the formula (VII)

ClCH$_2$—C(=O)—C(=N-OCH$_3$)—CONH—[cephem ring]—S—[furyl]

herein referred to as the chloro intermediate has also been prepared starting from 4-chloro-2-methoxyimino-3-oxobutyric acid and constitutes the novelty of this invention. This is also cyclized to yield ceftiofur sodium.

The examples below illustrate our invention without limiting the scope in spirit and content. The examples are described as two stage processes where the first stage forms the preparation of the inventive intermediate, and the second stage is the conversion to ceftiofur sodium.

EXAMPLE 1

Stage 1

Step A: Silylation of Furaca (Solution A)

To a suspension of Furaca (3.4 g, 0.01 moles) in methylene chloride (35 ml) at room temperature, added monotrimethylsilyl acetamide solution (3.94 g, 0.03 moles), catalytic amount of imidazole and stirred for 1 h 15 min to get a clear solution. This solution is cooled to −20 to −24° C. until use.

Step B: Preparation of 4-bromo-2-methoxyimino-3-oxobutyryl chloride (Solution B)

4-bromo-2-methoxyimino-3-oxobutyric acid (2.57 g) is added to methylene chloride (20 ml) and the solution is cooled to −20° C. Phosphorous pentachloride (2.5 g) is added in small lots over a period of 5 min while maintaining the temperature between −20° C. and −15° C. Thereafter, the temperature is slowly raised to −5° C. and the reaction mass is stirred at −5° C. to 0° C. until the starting material's absence is noted with TLC in about 30 mins. Aqueous workup was done to remove inorganic impurities and byproducts and the organic layer was dried over anhydrous sodium sulfate. This solution is taken as is for the next stage.

Step C: Preparation of the bromo intermediate

Solution B is added to solution A, while maintaining the temperature below −18° C. in a period of about 5 minutes. The temperature of the reaction mass is allowed to rise to −10° C. to −5° C. and the stirring is continued until the starting material, Furaca is less than 2% by HPLC analysis. Chilled water (35 ml) is added and the reaction mass is stirred at 3–5° C. for 10 min and the suspension filtered. Organic layer is separated and stirred at 3–5° C. whereupon the bromo intermediate precipitates out. The filtered solid is stirred for 1 h at 3–5° C., filtered, washed with methylene chloride and dried to yield 3.6 g of the bromo intermediate having a purity of >93% by HPLC analysis. (65.9% of theory). The structure is confirmed by spectroscopic data.

$^1$H NMR(300 MHz) (DMSO-d$_6$) delta: 3.57 (dd,2H, SCH$_2$), 4.11 (dd,2H,CH$_2$SCO), 4.04 (s,3H,OCH$_3$), 4.64(s, 2H, CH$_2$-Br), 5.14(dd,1H,6-H,J=4.85 Hz), 5.78 (dd,1H,7-H, J=4.78 Hz,8.24 Hz), 6.77 (dd,1H,Furyl-H), 7.44(d,1H, Furyl-H), 8.06(d,1H,Furyl-H), 9.46(d,1H,CONH J=8.38 Hz)

IR: (KBr) cm$^1$: 1780.6, 1722.8, 1659, 1631, 1595

Mass (Positive Ion Mode): 546, 548(M+1), 563, 565(M+Na) corresponding to $^{35}$Cl, $^{37}$Cl isotopes.

Stage II

Preparation of ceftiofur sodium

A solution of Bromo intermediate (3 g, 5.49 m. moles) in teterahydrofuran (7.5 ml) is added to a mixture of water (15 ml), tetrahydrofuran (7.5 ml), thiourea (0.63 g, 8.29 m. moles) and sodium acetate trihydrate (3 g, 22 m. moles) at 10° C. over a period of about 15 min. pH drops slowly to 5.5–6.0. The reaction mass is stirred until the HPLC analysis confirms the disappearance of the starting material in about 4–5 hours. Sodium chloride is added and the pH lowered to 3.0 by the addition of conc. Hydrochloric acid. The Tetrahydrofuran layer is separated, treated with activated carbon and converted into ceftiofur sodium by adding sodium 2-ethylhexanoate (5.5 g, 24.6% w/w solution in THF). The precipitation of ceftiofur sodium is carried out by adding the solution to tetrahydrofuran (80 ml). The precipitated solid is filtered, washed with acetone(20 ml) and dried to get 2.7 g of ceftiofur sodium (90% of theory).

$^1$H NMR (300 MHz) (DMSO-d6) delta: 3.32(dd,2H, SCH$_2$) 3.83(s,3H,OCH$_3$), 4.1(dd,2H,CH$_2$SCO), 4.98(d,1H, 6-H), 5.55(dd,1H,7-H), 6.73(s,1H,thiazolyl-H), 6.75(dd, 1H, Furyl-H), 7.23(s,2H,NH$_2$), 7.38(d,1H,Furyl-H), 8.03(s, 1H,Furyl-H), 9.52(d,1H,CONH)

Mass(Positive Ion Mode): 524(M+H), 546(M+Na)

EXAMPLE 2

Stage 1

Step A: Preparation of 4-bromo-2-methoxyimino-3-oxobutyrl chloride 4-bromo-2-methoxyimino-3-oxobutyric acid (14.8 g, 0.066 moles) is dissolved in methylene chloride (90 ml) at 0° C. This solution is cooled to −20° C. and to it is added N,N-Dimethylformamide (4.92 g). Oxalyl chloride (8.55 g, 0.067 moles) is added slowly maintaining the temperature at −20° C. to −18° C. The reaction mixture is stirred for 45 min at −15° C. to −20° C. to ensure completion of the reaction. The resulting product 4-bromo-2-methoxyimino-3-oxobutyryl chloride is taken as is for the step of condensation.

Step B: Prep of silylated Furaca

Furaca (20.4 g, 0.06 moles) is suspended in methylene chloride (120 ml) at 25° C. and to it is added trimethylsilylacetamide solution in methylene chloride (90ml containing 23.6 g of trimethylsilylacetamide; 0.18 moles). Stirring the reaction mass at 25° C. for 75–90 min resulted in a clear solution containing silylated Furaca. The reaction mass is cooled to −20° C. and to is added acetamide (10.62 g).

Step C: Preparation of the Bromo intermediate

4-Bromo-2-methoxyimino-3-oxobutyryl chloride prepared in Step A above is added to silylated Furaca made in Step B above at −18° C. to −20° C. in a period of about 10 min. The temperature of the reaction mass is slowly raised to −5° C. to −10° C. and stirred for 1 hour at this temperature. Thereafter cold water (180 ml, 5° C.) is added to the reaction mass and stirred at 2° C.–3° C. for about 5 min and the suspension is clarified. Separated the organic layer and extracted aqueous layer with methylene chloride (20 ml). Combined organic layer is washed with cold water (150 ml, 5° C.) and the organic layer is stirred at 2–5° C. Bromo intermediate precipitates within 5 min. Continued stirring at 2–5° C. for 30 min and filtered the solid. The product is successively washed with cold water (40 ml, 5° C.) followed by methylene chloride (40 ml) and dried under reduced pressure to get 25 g of bromo intermediate (75% of theory).

STAGE II

Preparation of ceftiofur sodium

The bromo intermediate obtained in Stage I steps above is converted into ceftiofur sodium by following the procedure outlined in the corresponding step of the previous Example 1.

EXAMPLE 3

Phosphorous oxychloride(11.13 g, 0.073 moles) is added slowly to a mixture of N,N-Dimethylformamide(5.96 g, 0.081 moles) and methylene chloride (110 mil) at 5–10° C. The mixture is stirred at room temperature for 2 hours and cooled to 0° C. 4-Bromo-2-methoxyimino-3-oxobutyric acid (14.8 g) is added in small lots to Vilsmeier reagent and stirred for 1 hour at 3–5° C. TLC analysis showed a complete disappearance of the starting material. This acid chloride is used for preparing ceftiofur sodium as described in Example 1.

EXAMPLE 4

4-Chloro-2-methoxyimino-3-oxobutynic acid(2.06 g, 0.0115 moles) is dissolved in methylene chloride (20 ml) and cooled to −20° C. Phosphorous pentachloride (2.5 g, 0.012 moles) is added in small lots over a period of about 5 min and the temperature of the reaction mass is allowed to rise to −5° C. to −2° C. Stirring is continued for 45 min for completion of the reaction. Cold water (10 ml, 5° C.) is added, separated the organic layer and dried over sodium sulfate. This acid chloride is reacted with silylated Furaca (3.4 g) as per procedure given in Example 1 to get the chloro intermediate 7-[4-chloro-2methoxyimino-3-oxobutyramido]-3-[2-furylcarbonylthio thyl]-3-cephem-4-carboxylic acid with a yield of 3 g (60% of theory) and an HPLC analyzed purity of 95%.

The analytical data corresponds to the proposed structure:

$^1$H NMR (300 MHz) (DMSO-d$_6$) delta: 3.57(dd,2H, SCH$_2$), 4.10(dd,2H,CH$_2$-S), 4.04(s,3H,OCH$_3$), 4.85(s,2H, CH$_2$-Cl), 5.15(d,6-H,J=4.85 Hz), 5.79(dd,1H,7-H,J=4.82 Hz, 8.35 Hz), 6.77(dd,1H, Furyl-H, J=1.67, 3.62 Hz), 7.44 (d,1H,Furyl-H, J=3.61 Hz), 8.06(d,1H,Furyl-H,J=1.03 Hz), 9.45(d,1H,CONH,J=8.36 Hz)

Mass spectrum Negative Ion Mode): 500(M-1)

The chloro intermediate is converted into ceftiofuir sodium by following the same corresponding procedure shown in Example 1 in 85% yield.

We claim:
1. A process for making a bromo intermediate for use in the manufacture of sodium ceftiofur comprising the steps of:

starting with the compound Furaca of the formula

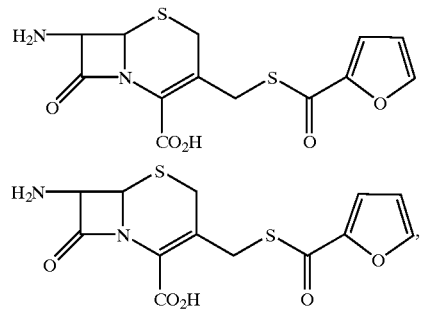

carrying out a silylation reaction of the said compound Furaca to produce a silylated Furaca, condensing the said silylated Furaca with the 4-bromo-2methoxyimino-3- oxoboxybutyric acid or its acid halide, isolating a bromo intermediate of the formula

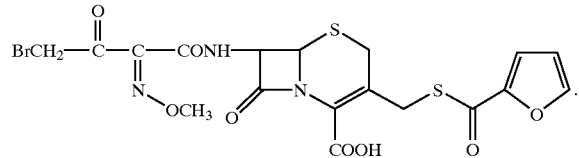

2. The process of claim 1, wherein the said acid halide is an acid chloride.

3. The process of claim 1, wherein the said acid halide is an acid bromide.

4. A process for making a chloro intermediate for use in the manufacture of sodium ceftiofur comprising the steps of:

starting with the compund Furace of the formula

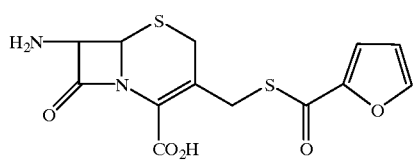

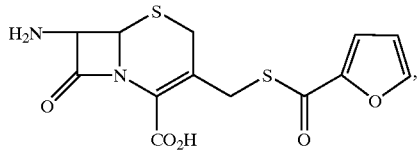

carrying out a silylation reaction of the said compound Furaca to produce a silylated Furaca, condensing the said silylated Furaca with the 4-chloro-2methoxyimino-3- oxoboxybutric acid or its acid halide, isolating a chloro intermediate of the formula

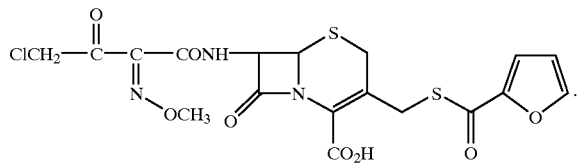

5. The process of claim 4, wherein the said acid halide is an acid chloride.

6. The process of claim 4, wherein the said acid halide is an acid bromide.

7. A process for making ceftiofur of the formula

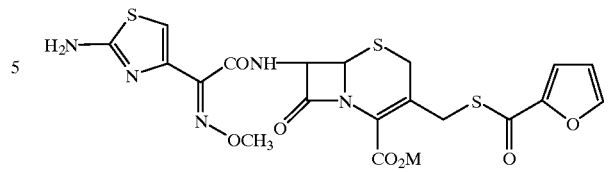

where M is H or Na, comprising of the steps of:
starting with the compound of the formula

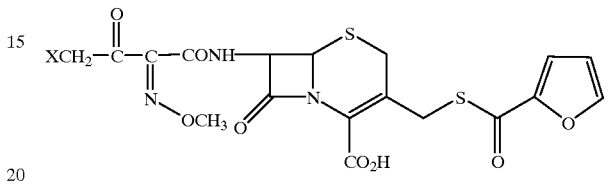

where X is Cl or Br,
carrying out the cyclization reaction of the said compound with thiourea in a solvent or a mixture of solvents,
isolating ceftiofur or its sodium salt.

8. The process as claimed in claim 7, where in the said solvent or said mixture of solvents is selected from the group consisting of ethanol, tetrahydrofuran and water.

9. A compound of the following formula useful in the preparation of Ceftiofur

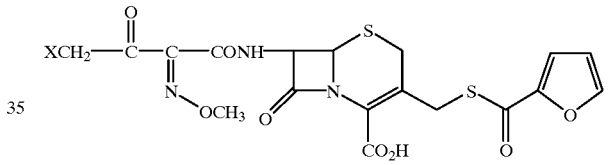

where X is Cl or Br.

* * * * *